United States Patent [19]

Hanson

[11] Patent Number: 5,154,607
[45] Date of Patent: Oct. 13, 1992

[54] LOW FRICTION ORTHODONTIC BRACKETS

[76] Inventor: G. Herbert Hanson, 57 Augusta Street, Hamilton, Ontario, Canada, L8N 1P8

[21] Appl. No.: 699,115

[22] Filed: May 13, 1991

[51] Int. Cl.⁵ ............................................. A61C 3/00
[52] U.S. Cl. ......................................................... 433/8
[58] Field of Search .................... 433/8, 10, 15, 13, 16, 433/18

[56] References Cited

U.S. PATENT DOCUMENTS

| | | | |
|---|---|---|---|
| 2,713,720 | 7/1955 | Johnson | 433/15 |
| 4,639,218 | 1/1987 | Jones et al. | 433/8 |
| 4,842,512 | 6/1989 | Kesling | 433/8 |
| 5,030,089 | 7/1991 | Kawaguchi | 433/8 |
| 5,062,794 | 11/1991 | Muira | 433/8 |

Primary Examiner—Cary E. O'Connor
Attorney, Agent, or Firm—Rogers & Scott

[57] ABSTRACT

Orthodontic brackets comprise a bracket body having a single centrally-disposed pair of gingivally-occlusially extending tie wings that protrude labially from the body and are embraced by a ligating loop to hold the bracket on the cooperating arch wire that passes through the arch wire slot, the slot thereby being of dual depth across the width of the bracket. The parts of the loop alongside the tie wings close the labial side of the slot but cannot engage a wire in the slot of smaller lingual-labial dimension than the slot, so that sliding friction between the wire and bracket is minimized. Such single central wings can be relatively wide in a small bracket, making it especially suited for production from ceramic materials. Another embodiment intended for manufacture from metal employs two mesially-distally spaced pairs of headed posts in place of the tie wings, each pair extending respectively from the gingival and the occlusal surface of the bracket body. A ligating loop can embrace one pair of the posts or all of the posts; the parts of the loop between the posts close the labial side of the arch wire so that the bracket can be operative with minimum friction, as with the tie wing structure.

13 Claims, 4 Drawing Sheets

LOW FRICTION ORTHODONTIC BRACKETS

FIELD OF THE INVENTION

This invention is concerned with improvements in or relating to orthodontic brackets, and especially to such brackets that permit minimisation of friction between the brackets and the cooperating arch wire.

REVIEW OF THE PRIOR ART

It has been a constant endeavour in the field of orthodontics to simplify and expedite the procedures that are employed for the sake of minimising the time taken by the procedures, which also leads to economy and reduction of discomfort to the patient. To this end there is substantial and continuing interest in bracket designs that for some procedures, or some stages of some procedures, enable the sliding friction between the bracket and the arch wire with which the bracket cooperates in moving the teeth to be minimized, if not completely removed.

It has also been an objective to make the brackets employed as small as possible, so as to make them as inconspicuous as possible in the patient's mouth, and also to reduce as much as possible potentially irritating engagement of the brackets with the soft tissues of the mouth and tongue. Hitherto orthodontic patients overwhelmingly have been children, but in recent years the number of adult patients has increased considerably. Adults requiring the procedure for themselves are much more concerned than are the parents of a child about the cosmetic appearance in the mouth of the brackets and their connecting arch wires.

One way in which cosmetic appearance can be improved is by use of the so-called "lingual" technique, in which the brackets are mounted on the lingual surfaces (backs) of the teeth, and hence concealed from view. A disadvantage is that the brackets and wires are very readily contacted by the tongue, and it is important therefore that the brackets be as small as possible and free from any rough edges that would irritate the tongue.

Another approach is to mount the brackets on the labial surfaces, but to make them of transparent material, or of a material, such as a ceramic or plastics material, that has been colored to approximate the tooth color. The choice of suitable materials for this purpose is difficult because of the surprisingly high stresses to which the brackets are subjected in normal use. It is fortunate that the inherently small size of orthodontic brackets, and consequently small amounts of material required for their fabrication, makes it possible to use materials that are relatively expensive. An example of such transparent materials that have been proposed are single crystal alpha alumina or sapphire, as disclosed in U.S. Pat. No. 4,639,218, issued to Johnson & Johnson Dental Products Company. These ceramic materials, although strong, are brittle and still have strength moduli that are only a fraction of those of the available metals, so that inherently it has not previously been possible to make them as small as an equivalent metal bracket.

If metal is not to be used in the brackets then, owing to the insufficient or almost complete absence of suitable elastic properties in these alternative materials, it is not possible to provide retaining springs in the brackets, as are required for example by my prior brackets, as disclosed for example in my U.S. Pat. Nos. 3,772,787; 4,248,588; and 4,492,573. Instead it is necessary to revert to the prior techniques employing elastomeric loops and/or tie wires to retain the arch wire in the arch wire slot, despite the comparative inefficiency of installation and subsequent operation of such techniques.

DEFINITION OF THE INVENTION

It is therefore a principal object of the present invention to provide new orthodontic brackets with which sliding friction between the bracket and a cooperating arch wire can be minimised.

It is another principal object to provide brackets that can be made of very small dimensions as compared to equivalent brackets used hitherto and employing ligating loops and ties.

It is a further object to provide such new brackets that are particularly suited for manufacture from non-metallic, cosmetically-desirable materials, such as transparent and tooth-coloured ceramic materials.

In accordance with the present invention there is provided an orthodontic bracket comprising:

a bracket body having labial, lingual, gingival, occlusal and mesial/distal surfaces;

the body having therein a mesial-distal extending arch-wire-receiving dual depth slot having gingival, lingual and occlusal side walls and opening at its labial side to the said labial surface;

the body having protruding from its labial, gingival and occlusal surfaces, and disposed at least approximately centrally of the length of the body, a pair of opposed gingival-occlusal-extending tie-wing portions for the reception and retention of a ligation loop;

the central portion of the body including the tie-wing portions thereby being of greater labial-lingual depth than the two side portions of the body on the respective sides of the said central portion, and being of a mesial-distal width that is between 30% and 50% of the overall mesial-distal width of the bracket body;

the two side portions providing respective mesial-distal extending side portion labial surfaces against which a ligation loop embracing the tie-wing portions engages, whereby the portions of a ligation loop extending over the respective portions of the arch wire slot labial side openings are held by said side portion labial surfaces spaced corresponding distances from the lingual wall of the slot;

the arch wire slot extending between and separating the tie wing portions, a central portion of the slot in the said central portion of the body thereby also being of greater labial-lingual depth than the side portions of the slot in the said side portions of the body, said central portion of the slot having its opposed gingival and occlusal surfaces parallel to one another across the full extent of its width within the body, and having its opposed gingival and occlusal surfaces parallel to one another across a substantial extent of its width between the tie wing portions.

Also in accordance with the invention there is provided an orthodontic bracket comprising:

a bracket body having labial, lingual, gingival, occlusal and mesial/distal surfaces;

the body having therein a mesial-distal extending arch-wire-receiving slot having gingival, lingual and occlusal side walls and opening at its labial side to the said labial surface;

the body having protruding from its gingival and occlusal surfaces two mesially-distally spaced pairs of gingivally- and occlusially-extending headed posts, each pair extending from a respective side portion of the bracket body;

the two side portions providing respective mesial-distal extending side portion labial surfaces against which a ligation loop embracing the posts engages, whereby the portions of a ligation loop extending over the respective portions of the arch wire slot labial side openings are held by said side portion labial surfaces spaced corresponding distances from the lingual wall of the slot.

Preferably the central portion of the body is of greater labial-lingual depth than the two side portions of the body on the respective sides of the said central portion;

the central portion of the slot in the said central portion of the body thereby also being of greater labial-lingual depth than the side portions of the slot in the said side portions of the body.

Preferably also the central portion of the bracket body is of a mesial-distal width that is between 20% and 30% of the overall mesial-distal width of the bracket body.

DESCRIPTION OF THE DRAWINGS

Particular preferred embodiments of the invention will now be described, by way of example, with reference to the accompanying diagrammatic drawings, wherein.

DESCRIPTION OF THE PRIOR ART

Throughout the description which follows, and also in the claims to avoid awkwardness in language, the brackets, the ligating loops and their operation and installation will be described as they are employed in the conventional labial technique. The manner of their corresponding employment in lingual techniques will be apparent to those skilled in this particular art.

Figure 1:
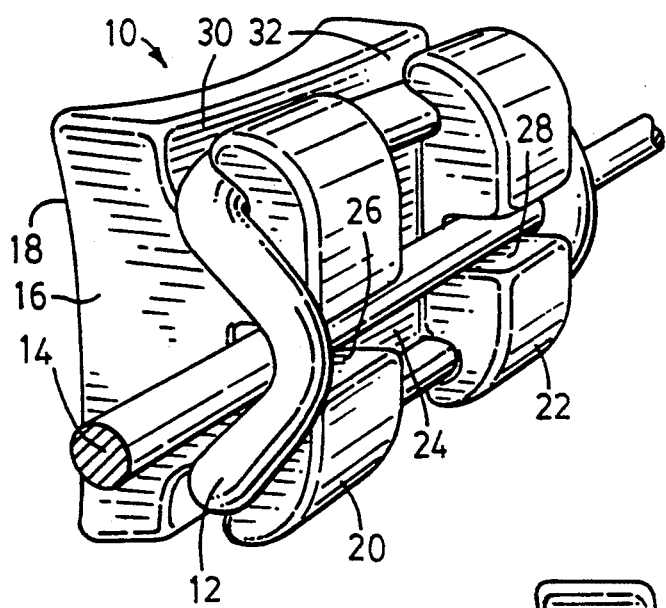
FIG. 1 is a perspective view toward the lingual of a prior art edgewise bracket, and illustrating the manner of the retention of an arch wire in the slot thereof by a ligating loop or elastomeric material.
Figure 2:
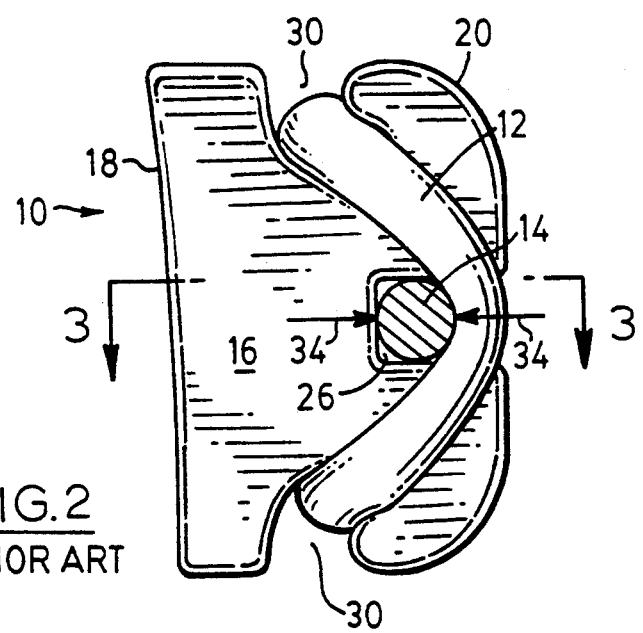
FIG. 2 is an end elevation of the arrangement of FIG. 1.
Figure 3:
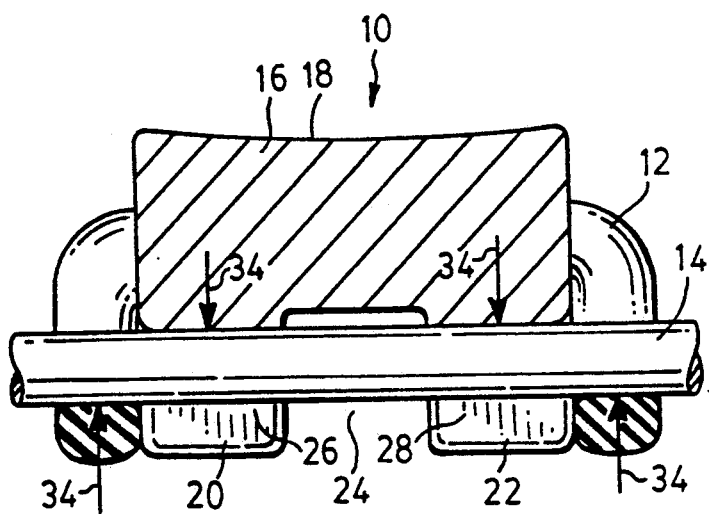
FIG. 3 is a cross-section taken on the line 3—3 of FIG. 2.

FIGS. 1 through 3 illustrates a typical prior art orthodontic edgewise technique bracket 10, as used hitherto in a labial system in conjunction with an elastomeric ligating loop 12 (or with a tie wire which is not illustrated) to connect the bracket to an arch wire 14 on which it is mounted. The wire may be of circular cross-section as illustrated, or of rectangular cross-section, which is not illustrated. Prior to the development of suitable ceramic materials these brackets were made of metal, usually stainless steel. Orthodontic brackets so far made from single crystal alpha alumina and polycrystalline ceramic materials have, as far as I am aware, and insofar as they have been described and illustrated in the above-mentioned U.S. Pat. No. 4,639,218, been designed to closely approximate this traditional configuration. Thus, the bracket consists of a body 16, the lingual face 18 of which is shaped to conform relatively closely to the labial tooth face to which it is to be applied. The body is provided at its ends with two mesially-distally spaced, occlusially-gingivially extending pairs of tie wings 20 and 22 having a space 24 between them; to avoid undesired rotations these two pairs of tie-wings are spaced mesially-distally as far apart as possible. Each pair is provided with a respective central arch-wire-receiving slot 26 and 28 opening to the labial surface, of rectangular cross-section, and essentially of uniform depth throughout its mesial-distal width, i.e. its cross-sectional geometry does not vary along its mesial-distal dimension. The tie wings extend gingivally and occlusially to about the same height as the body 16 and are provided with respective mesially-distally-extending, gingivally, and occlusally-opening, ligature-receiving slots 30 and 32; these slots undercut labially a substantial distance into the tie wings to ensure that the ligature will not slip off the bracket if it should become flaccid in use.

The ligature 12 is of typical prior art construction and consists of an elastomeric ring (i.e. a toroid) of circular transverse cross-section; it will be observed that the ligature-receiving slots 30 and 32 are disposed considerably closer, by about their own labial-lingual depth, to the body lingual face 18 than are the lingual faces of the slots 26 and 28; the purpose of this particular bracket geometry is to permit the ligature to press an undersize arch wire into contact with the slot lingual walls for control of tooth rotation about the occlusial-gingival axis.

This traditional bracket and ligating loop structure has been found to have disadvantages; for example the tie-wings extend mesially and distally to the same extent as the slots 26 and 28, and this sometimes prevents the brackets from being positioned far enough in the mesial or distal direction on a tooth that is severely rotated because of engagement and interference of the bracket with the immediately adjacent tooth. The relative placement of the ligature slots 30 and 32 and the respective arch wire slots 26 and 28 means that there is always constant engagement of the lingual slot face with the wire under the pressure that is provided by the ligature loop 12, and consequently there is always considerable frictional resistance to sliding movement of the bracket 10 along the arch wire 14. The counteracting forces resulting from this pressure and produced by the elastic ligature loop are indicated in FIGS. 2 and 3 by arrows 34. This relatively high frictional resistance is counterproductive in that it opposes the sliding movements along the arch wire that are necessary for efficient tooth movement and alignment. Another problem that is exacerbated by the relatively low strength moduli of currently available non-metallic bracket materials is that the tie wings are weakened by their extended length, and by the undercuts, resulting in relatively frequent breakage of the wings from the bracket body to the detriment of the procedure and inconvenience to the patient, plus the danger that the fragments may be aspirated or swallowed.

DESCRIPTION OF THE PREFERRED EMBODIMENTS

A bracket 36 which is a first embodiment of the invention, as illustrated by FIGS. 4-7, consists of a bracket body having a lingual face 38 also shaped to conform as closely as possible to the tooth face (not shown), either labial or lingual, to which it is to be applied. The bracket body is provided with a single pair of occlusally-gingivally-extending tie wing portions 40 and 42 disposed at least approximately at the center of the width of the bracket body and protruding from its labial, gingival and occlusal surfaces, so that this central portion of the body is of greater labial-lingual depth than the two side portions that constitute the remainder thereof. These tie wing portions are of a mesial-distal width that is a minor portion, from about 30% to about 50%, of the overall mesial-distal width of the bracket body, usually about 40% thereof. A labially-opening arch wire slot 44 extends the full mesial-distal width of the bracket body and separates the two tie wings. The central portion of this slot in the central portion of the bracket body is of rectangular cross-section and is of greater labial-lingual depth than the adjoining two slot side portions, which in this embodiment are of square cross section. The resulting dual depth slot is continuous throughout the width of the bracket body with its lingual, gingival and occlusal surfaces smooth continuations of one another. The single central pair of tie wings 40 and 42 are slightly shorter than those of the prior art bracket in the gingival-occlusal direction and are thicker in the lingual-labial direction, so as to have larger "root areas" where they join the bracket body, making them relatively much stronger and less likely to be broken off by fracture. The lingual faces 50 of the tie wings are "raked" in the lingual direction to facilitate retention of a ligature loop 46 that embraces them, but are not undercut as much as with the prior art brackets. The central location and the smaller size of the tie wings reduces the possibility of interference with adjacent or opposing teeth, even if such teeth are severely rotated from the normal position.

Figure 4:
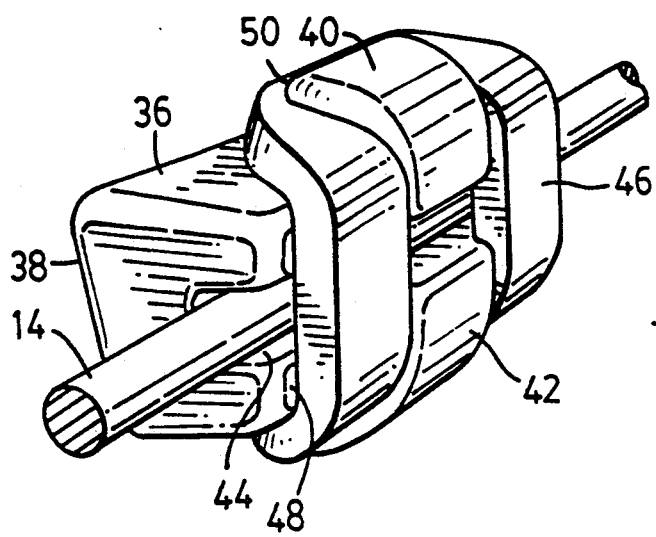
FIG. 4 is a perspective view similar to FIG. 1 of a bracket that is a first embodiment of the invention.
Figure 5:
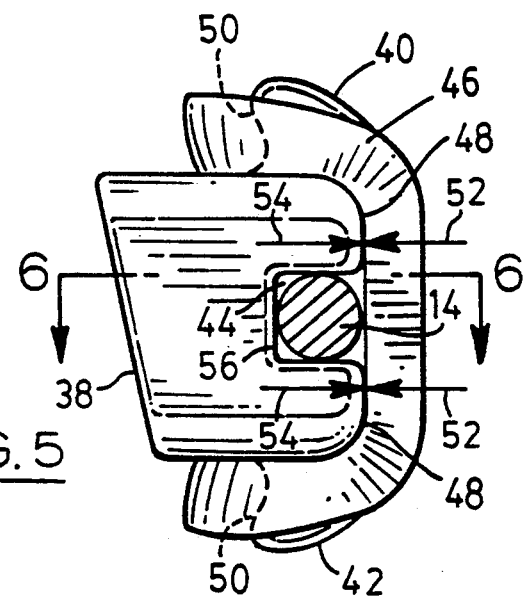
FIG. 5 is an end elevation of the embodiment of FIG. 4.
Figure 7:
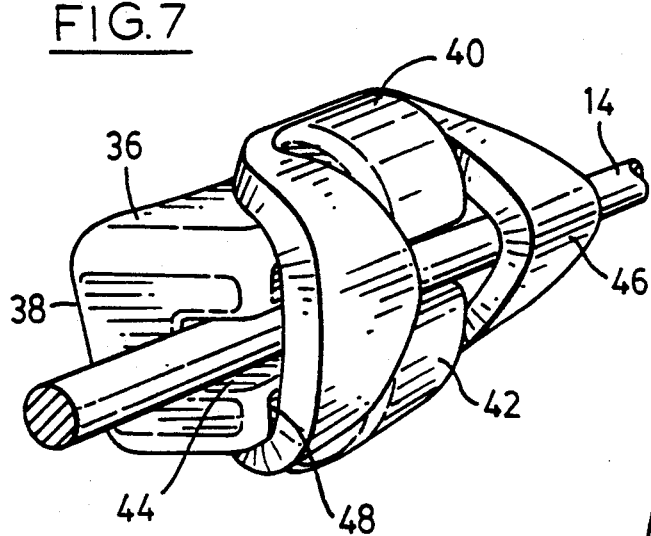
FIG. 7 is a perspective view similar to FIG. 4 of a second embodiment, and also illustrating the manner in which tooth rotation is obtained with the brackets of the invention.
Figure 10:
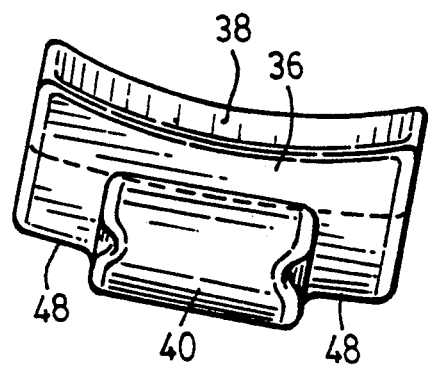
FIG. 10 is a top elevation, i.e. from the gingival, of the second embodiment.
Figure 8:
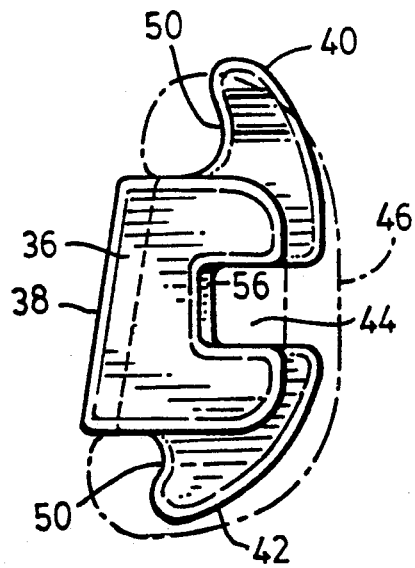
FIG. 8 is an end elevation similar to FIG. 5 of the second embodiment.
Figure 9:
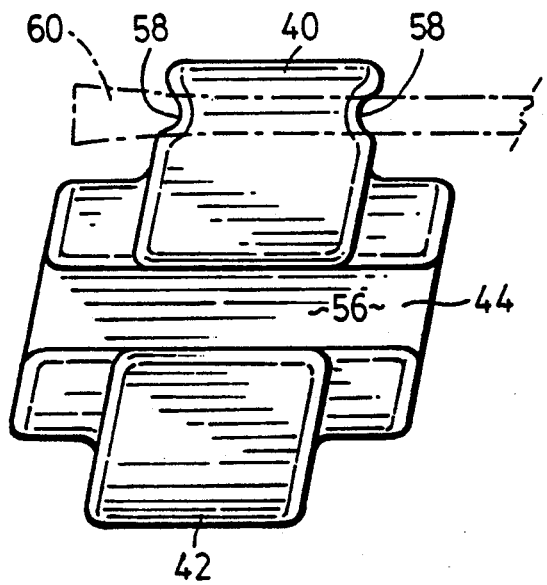
FIG. 9 is a front elevation, i.e. toward the lingual, of the second embodiment.

It will be noted from FIGS. 4 and 5 that the ligature loop 46 bears against the labial faces 48 of the bracket body side portions and against the lingual faces 50 of the tie wings 40 and 42, but cannot engage the arch wire 14 unless the latter is so large in its labial-lingual depth dimension that it protrudes from the slot, or unless the tooth to which the bracket is attached is rotated to an extent that the wire protrudes from one end of the slot, as illustrated by FIG. 7. The forces applied by the ligature against the bracket, and the reaction of the bracket, are therefore as indicated respectively by the arrows 52 and 54 in FIG. 5. The ligature closes the two side portions of the arch-wire slot and forms a rigid barrier to arch wire escape to the labial, but still permits unimpeded, virtually friction-free, mesial-distal sliding movement of the bracket along the wire, as is preferred for many procedures. Such friction-reduced sliding is obtained however tightly the ligation loop embraces the tie wings, so that there is no need for relatively critical adjustment of its tension during installation, and there is much greater latitude for extension while in use before the loop becomes so flaccid that there is danger of it releasing from the bracket. If resistance against such sliding movement is required it can be obtained as described below. However, the smaller size arch wires that are often used in the first stages of a procedure can work more efficiently because of the absence of significant frictional binding.

Owing to its smaller more compact structure this new bracket is more cosmetically desirable, and, also because of this compact structure, is structurally relatively stronger than the above-described prior art bracket. It therefore is particularly suited for manufacture from ceramic materials, such as any one of a polycrystalline ceramic, single crystal alpha alumina, sapphire, or cubic zirconia (which is tougher than sapphire). A particularly suitable material for such "cosmetic" brackets is white nephrite or jadite, particularly the translucent, so-called "mutton-fat" white nephrite or jadite., which have a particular interlocked crystal structure rendering them more resistant to fracture than the single crystal materials.

Although it is not possible to make these new brackets as small as some of my prior art metal brackets, for example those disclosed in my U.S. Pat. No. 4,698,017, it is possible to make them of considerably smaller size than the above described prior art brackets when made of non-metallic materials. In particular embodiments the total height of the bracket at the tie wing portions is 2.77-3.04 mm (0.109-0.120 in), while the height at its side portions is about 1.65 mm (0.065 in); the overall mesial-distal width is about 2.54-3.05 mm (0.100-0.120 in), while the central tie wing portion is about 1.12 mm (0.044 in) wide. The labial-lingual depth varies of course, depending upon the tooth to which it is to be applied. The said "rake" of the faces 50 is about 20° and will vary between 15° and 25°. The side portions of the slot of square cross-section will be either 0.56×0.56 mm (0.022×0.022 in) or 0.61×0.61 mm (0.024×0.024 in), while the central rectangular cross-section portion will be respectively 0.56×0.86 mm (0.022×0.034 in) or 0.61×0.86 mm (0.024×0.034 in). Procedures which require the bracket to slide freely along the wire can be carried out with the smaller slot, with no significant frictional drag, by using high-modulus wires that are 0.50 mm (0.020 in) round, 0.050×0.50 mm (0.020×0.020 in) square or half-round/half square. The comparable wire dimensions for the larger slot size are 0.56 mm (0.022 in) round and 0.56×0.56 mm (0.022×0.022 in) square and half-round/half square.

If heavier torque forces are required to tip the teeth rectangular wires may be used that more fully fill the deeper central portion of the slot and protrude labially from the slot side portions. These will then bind in the slots under the lingual urge (arrows 52) of the ligature 46 and mesio-distal sliding along the wires will be impeded, as with the prior art brackets. Typically these heavier torques are required only for the upper incisors to prevent them from tipping as they are being retracted lingually. An excellent way of accomplishing this is to use a dual dimension arch wire as disclosed by Art Wool in U.S. Pat. No. 4,479,779; such an arch wire has an anterior portion of rectangular cross-section and posterior portions of round cross-section, the rectangular anterior part of the wire engaged in the slot generating a strong counter-moment in the brackets attached to the incisors to oppose tipping, while the round posterior parts are free to slide distally through the aligned slots in the brackets attached to the canines, bicuspids and molars. In some procedures it is found that square and half-round/half-square wires generate a sufficiently high torque couple, so that heavy frictional binding can be totally avoided. A dual dimension wire can be used in which the posterior portion is square or half-square/half-round, thereby giving some torque control to the posterior teeth without generating the usual frictional resistance to sliding; this is more often required in the lower arch to help prevent lingual collapse during closure of a gap resulting from extraction. The bracket therefore permits more efficient tooth movement without sacrificing attitude control.

Figure 6:
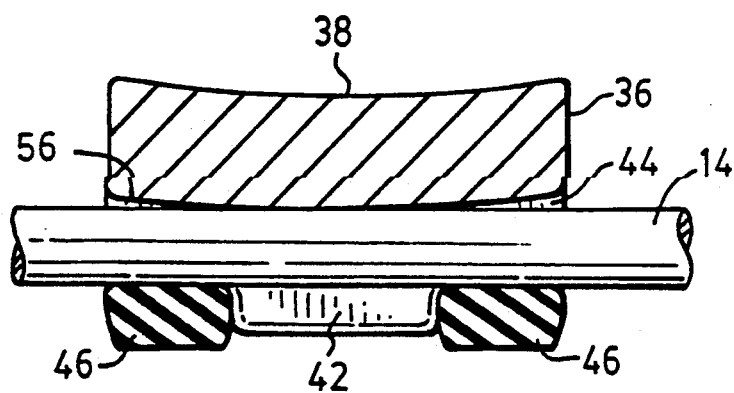
FIG. 6 is a cross-section taken on the line 6—6 of FIG. 5.

As is most clearly seen in FIG. 6, the lingual face 56 of the slot is made convex in the labial direction on a relatively large radius (in this embodiment 25.4 mm (1.00 in); preferably the labial faces of the body side portions are also formed to the same radius so that the surface 56 is smoothly continuous. A suitable range for this radius is from 17.78 mm (0.70 in) to 47.0 mm (1.85 in). Brackets for use in the lingual techniques would require these surfaces to be concave for the anterior teeth and flat for the posterior teeth. This gives the bracket a greater "self-centering" facility in rotation from a relatively extreme position as shown in FIG. 7, this Figure illustrating a case where the tooth to which the bracket is attached requires relatively considerable rotation, to the extent that the arch wire protrudes from the respective slot side portion. When the slot lingual surface is formed with a curvature in this manner the labial faces of the body side portions will usually be formed to the same radius.

A second embodiment of the invention is shown in FIGS. 7 through 10 and is functionally similar to that of FIGS. 4 through 6. The gingivally-extending tie wing portion 40 is made somewhat longer gingivally than the tie wing portion 42 and is provided in its two mesial-distal side surfaces with shallow recesses 58 that receive and facilitate the retention of an elastomeric ribbon 60 used as a tension member to connect the bracket to another bracket or to some other suitable anchor point in the patient's mouth. A ribbon that is particularly suited for this purpose is disclosed in my prior application No. 07/661,969, filed Feb. 28, 1991, the disclosure of which is incorporated herein by this reference. As is seen particularly in FIG. 9 the bracket body is made to a rhombic shape as seen from the labial-lingual, instead of rectangular as with the prior art brackets of FIGS. 1-3 and the first embodiment of FIGS. 4-6, and this rhombic shape is found to be advantageous to the orthodontist in facilitating the accurate occlusal-gingival alignment of the brackets as they are placed on the teeth. The first embodiment of FIGS. 4-6 can also be made to this rhombic shape.

Figure 12:
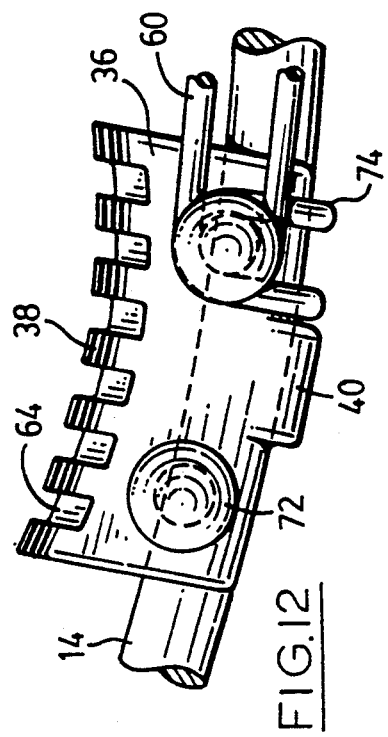
FIG. 12 is a view similar to FIG. 10 of the third embodiment.
Figure 11:
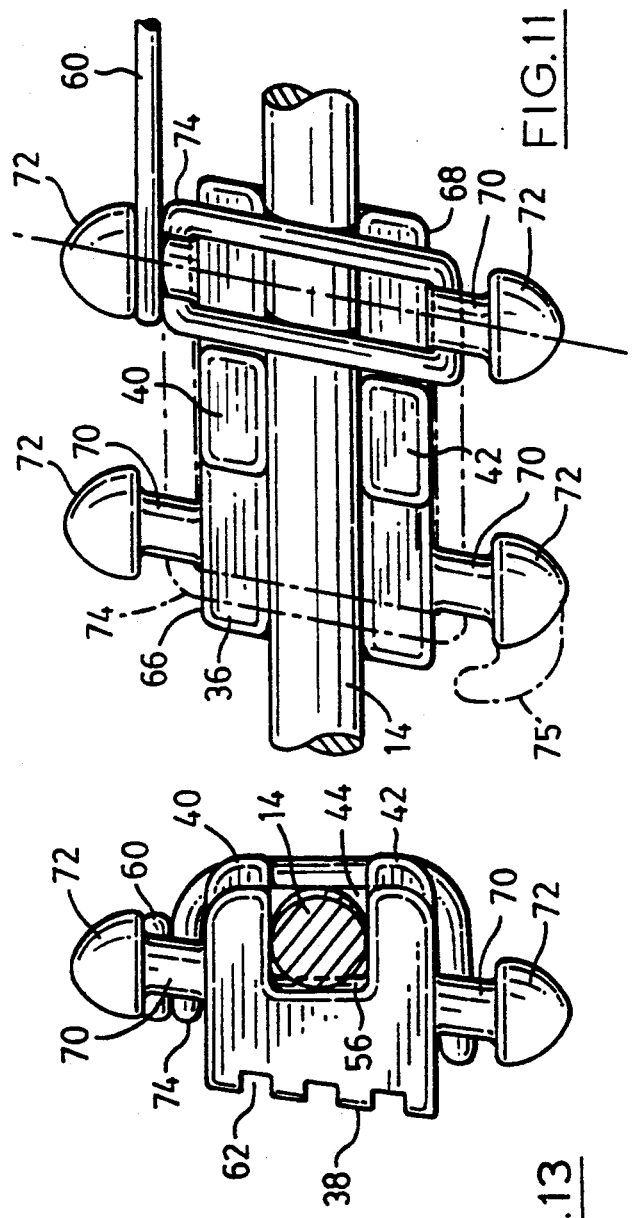
FIG. 11 is a similar view of FIG. 9 of a third embodiment.
Figure 13:
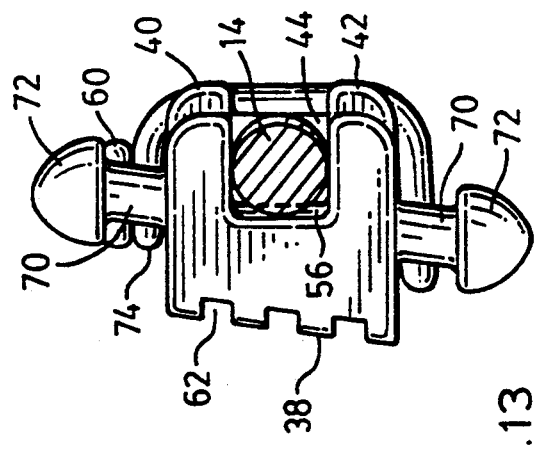
FIG. 13 is a view similar to FIG. 8 of the third embodiment.

In the embodiment of FIGS. 11-13, which is particularly intended for manufacture in metal, such as 17-4 PH stainless steel, the lingual surface 38 is provided with a first series of mesially-distally extending slots 62, and a second series of gingivally-occlusally extending slots 64, so as to provide ample space for the reception of a cement by which the bracket is attached to the tooth. These relatively large open periphery slots also facilitate light transmission for deep curing of light cured adhesives when used to attach the brackets to the teeth. The bracket body also has the rhombic shape of that of the bracket of FIGS. 7-11, but in this embodiment the two gingivally and occlusally extending portions of the tie wings 40 and 42 are absent, so that the corresponding mesially-distally-extending gingival and occlusal surfaces 66 and 68 respectively are now continuous across the full width of the bracket body; the labially protruding central portions 40 and 42 still remain. Each side portion of the bracket body is provided with two gingivally-occlusially-extending mushroom-headed post members, each extending from the respective gingival surface 66 or occlusal surface 68, and each comprising a post shaft 70 of reduced diameter that terminates in a mushroom shaped head 72.

As illustrated, each pair of posts at the same side portion of the bracket can be used as the anchor means for a respective ligation loop 74, which embraces the posts and is retained thereon by the heads, the selection of the pair to be used depending upon the requirements of the procedure. In some procedures two such loops may be used, one around each pair of posts, or a single loop may extend around all four posts, as shown in broken lines in FIG. 11. The length of the posts 70, at least of the two posts at the gingival side of the bracket, is such that they can accommodate both the ligation loop 74 and a tension connecting loop 60, for example of the kind referred to in my application identified above. As with the two previous embodiments, provided the arch wire 14 does not protrude from the slot the mounting of the bracket on the arch wire is achieved with the possibility of virtually frictionless sliding motion between them. In a modification of this embodiment one or more of the posts may be provided with a hook 75 (FIG. 11) that will serve as an anchor for another connecting means, such as intermaxillary latex elastics or tension spring. Ball-headed posts may be used instead of the mushroom headed posts illustrated, but the mushroom headed posts are preferred since the radially-extending flatter underside head surfaces provide more positive retention of the ligation loops.

In an embodiment which is not illustrated the body and the arch wire slot 44 are not of dual depth as in the two preceding embodiments, but are of constant depth over the full width of the bracket body. However the protrusions 40 and 42 and the dual depth slot are of value in that they make the bracket suitable in cooperation with a close-fitting rectangular wire for producing or inhibiting torquing or tipping movement of the teeth, i.e. rotation about a mesial-distal axis. The protrusions can in this embodiment be of narrower width than for the other embodiments and they will usually be of a width from about 20% to about 30% of the total width of the bracket body.

In a specific embodiment the shaft 70 is from 0.30 mm to 0.35 mm (0.012 in to 0.014 in) diameter, while the head is of 0.60 mm to 0.70 mm (0.024 in to 0.028 in) diameter. The overall length of the posts is from a shorter value of 0.68 mm (0.027 in) to a longer value of 0.9 mm (0.036 in).

I claim:

1. An orthodontic bracket comprising:
    a bracket body having labial, lingual, gingival, occlusal, mesial, and distal surfaces;
    the body having therein a mesial-distal extending arch-wire-receiving slot having gingival, lingual and occlusal side walls and opening at its labial side to the said labial surface;
    the body having protruding from its labial, gingival and occlusal surfaces, and disposed at least approximately centrally of the length of the body, a central body portion thereof including a pair of opposed gingival-occlusal-extending tie-wing portions for the reception and retention of a ligation loop;

the central body portion having therein a central slot portion and being of greater labial-lingual depth than the two side portions of the body on the respective sides of the said central portion, which body side portions have therein respective side slot portions, the central body portion being of a mesial-distal width that is between 30% and 50% of the overall mesial-distal width of the bracket body;

the two body side portions providing respective mesial-distal extending body side portion labial surfaces against which a ligation loop embracing the tie-wing portions engages, whereby the portions of a ligation loop extending over the respective openings of the side slot portions are held by said body side portion labial surfaces spaced corresponding distances from the lingual wall of the slot;

the two side slot portions being of square cross-section in a transverse gingival occlusal plane, and the central slot portion being of greater labial-lingual depth than the side slot portions so as to be of rectangular cross-section in the said gingival occlusal plane, the slot having its opposed gingival and occlusal surfaces parallel to one another across the full extent of its width within the body side portions and the intervening connecting part of the body central portion, and having its opposed gingival and occlusal surfaces parallel to one another across a substantial extent of its width in the labially protruding part of the body central portion.

2. A bracket as claimed in claim 1, wherein the lingual surface of the slot is formed on a relatively large radius about a gingivally-occlusially extending axis to be convex toward the labial surface of the bracket body.

3. A bracket as claimed in claim 2, wherein the labial faces of the body side portions are formed to the same radius as the slot lingual surface.

4. A bracket as claimed in claim 1, wherein the body is made of a material selected from the group consisting of polycrystalline ceramic, single crystal alpha alumina, sapphire, cubic zirconia, nephrite and jadite.

5. A bracket as claimed in claim 1, wherein the bracket body is of rhombic shape in the labial-gingival direction.

6. An orthodontic bracket as claimed in claim 1, wherein at least one distal face of the tie wing portions is provided with a respective mesially-extending recess for retaining reception of a ligation loop embracing the tie wing portions.

7. An orthodontic bracket comprising:
a bracket body having labial, lingual, gingival, occlusal and mesial/distal surfaces;

the body having therein a mesial-distal extending arch-wire-receiving slot having gingival, lingual and occlusal side walls and opening at its labial side to the said labial surface;

the body having protruding from its gingival and occlusal surfaces two mesially-distally spaced pairs of gingivally- and occlusially-extending headed posts, each pair extending from a respective side portion of the bracket body;

the two side portions providing respective mesial-distal extending side portion labial surfaces against which a ligation loop embracing the posts engages, whereby the portions of a ligation loop extending over the respective portions of the arch wire slot labial side openings are held by said side portion labial surfaces spaced corresponding distances from the lingual wall of the slot.

8. A bracket as claimed in claim 7, wherein the central portion of the body is of greater labial-lingual depth than the two side portions of the body on the respective sides of the said central portion;

the central portion of the slot in the said central portion of the body thereby also being of greater labial-lingual depth than the side portions of the slot in the said side portions of the body.

9. A bracket as claimed in claim 8, wherein the side portions of the slot in the body side portions are of square transverse cross-section, and the central portion of the slot in the body central portion is of rectangular transverse cross-section, the lingual, occlusal and gingival faces of the slot being smoothly coextensive with one another.

10. A bracket as claimed in claim 8, wherein the central portion of the bracket body is of a mesial-distal width that is between 20% and 30% of the overall mesial-distal width of the bracket body.

11. A bracket as claimed in claim 7, wherein the heads of the headed posts are of mushroom shape.

12. A bracket as claimed in claim 7, wherein the lingual surface of the slot is formed on a relatively large radius about a gingivally-occlusially extending axis to be convex toward the labial surface of the bracket body.

13. A bracket as claimed in claim 12, wherein the labial faces of the body side portions are formed to the same radius as the slot lingual surface.

* * * * *